United States Patent [19]

Lottick

[11] Patent Number: 5,116,332
[45] Date of Patent: May 26, 1992

[54] ELECTROCAUTERY HEMOSTAT

[76] Inventor: Edward A. Lottick, 789 Wyoming Ave., Kingston, Pa. 18704

[21] Appl. No.: 477,094

[22] Filed: Feb. 8, 1990

Related U.S. Application Data

[63] Continuation-in-part of Ser. No. 881,750, Jul. 2, 1986, Pat. No. 5,026,370, which is a continuation of Ser. No. 663,091, Oct. 24, 1984, abandoned, which is a continuation-in-part of Ser. No. 443,517, Nov. 22, 1982, Pat. No. 4,552,143, which is a continuation-in-part of Ser. No. 242,746, Mar. 11, 1981, Pat. No. 4,370,980.

[51] Int. Cl.$^5$ .............................................. A61B 17/36
[52] U.S. Cl. ........................................ 606/42; 606/49; 606/52
[58] Field of Search ................... 606/41, 42, 45, 39, 606/40

[56] References Cited

U.S. PATENT DOCUMENTS

| | | | |
|---|---|---|---|
| 164,183 | 6/1875 | Kidder | 128/303.1 |
| 371,664 | 10/1887 | Brannan et al. | 128/303.1 |
| 595,573 | 12/1897 | MacGregor | 128/303.14 |
| 702,472 | 6/1902 | Pignolet | 128/303.1 |
| 1,071,978 | 9/1913 | White | 128/303.13 |
| 1,813,902 | 7/1931 | Bovie | 128/303.14 |
| 2,002,594 | 5/1935 | Wappler et al. | 128/303.14 X |
| 2,120,598 | 6/1938 | Beuoy | 219/240 X |
| 2,176,479 | 10/1939 | Willis | 128/303.13 |
| 2,249,894 | 7/1941 | Goldenstein | 128/303.13 |
| 2,888,927 | 6/1959 | Fozard | 128/303.13 |
| 3,100,489 | 8/1963 | Bagley | 128/303.17 |
| 3,234,356 | 2/1966 | Babb | 128/303.1 |
| 3,643,663 | 2/1972 | Sutter | 128/303.17 |
| 3,752,160 | 8/1973 | Billin | 128/303.17 |
| 3,789,831 | 2/1974 | Kopaniky et al. | 128/692 |
| 3,801,766 | 4/1974 | Morrison, Jr. | 200/157 |
| 3,878,348 | 4/1975 | German | 200/157 |
| 3,911,241 | 10/1975 | Jarrard | 128/303.17 X |
| 3,938,527 | 2/1976 | Rioux et al. | 128/303.17 |
| 3,980,861 | 9/1976 | Fukunaga | 128/303.1 |
| 3,982,529 | 9/1976 | Sato | 128/641 |
| 4,005,714 | 2/1977 | Hiltebrandt | 128/303.17 |
| 4,032,738 | 6/1977 | Esty et al. | 128/303.13 X |
| 4,034,761 | 7/1977 | Prater et al. | 128/303.14 |
| 4,041,952 | 8/1977 | Morrison, Jr. et al. | 128/303.13 |
| 4,076,028 | 2/1978 | Simmons | 128/303.13 |
| 4,174,714 | 11/1979 | Mehl | 128/303.13 |
| 4,213,460 | 7/1980 | Weiner | 128/303.1 |
| 4,367,744 | 1/1983 | Sole | 128/303.1 |
| 4,370,980 | 2/1983 | Lottick | 128/303.17 |
| 4,375,218 | 3/1983 | DiGeronimo | 128/303.17 |
| 4,418,692 | 12/1983 | Guay | 128/303.14 |
| 4,443,935 | 4/1984 | Zamba et al. | 606/42 |
| 4,492,832 | 1/1985 | Taylor | 606/42 |
| 4,552,143 | 11/1985 | Lottick | 128/303.14 |

FOREIGN PATENT DOCUMENTS

| | | | |
|---|---|---|---|
| 305566 | 1/1952 | Denmark | 128/303.1 |
| 1803292 | 10/1968 | Fed. Rep. of Germany | 128/303.17 |
| 757933 | 1/1934 | France | 128/303.14 |
| 1536272 | 6/1967 | France | 128/303.17 |
| 575103 | 10/1977 | U.S.S.R. | 128/303.14 |
| 578972 | 11/1977 | U.S.S.R. | 128/303.14 |

OTHER PUBLICATIONS

Stevenson, "Combined Diathermy Forceps and Scissors", The Lancet, pp. 650-651, Oct. 24, 1959.
V. Rosenberg, "New Bipolar Forceps for Electrocoagulation", Plastic & Reconstructive Surgery, vol. 48, No. 4, 1964.

Primary Examiner—David M. Shay
Attorney, Agent, or Firm—Michael F. Petock

[57] ABSTRACT

Improved electrocautery instruments, particularly instruments better adapted for manufacture at lower costs, are disclosed including an electrocautery hemostat comprised of a hemostat provided with clam shell synthetic plastic handles with a switch incorporated therein. The mirror image plastic clam shells are mounted over the handle portion of the instrument and bonded together, preferably by sonically welding. Other embodiments include an instrument wherein a substantial or major portion of the instrument, particularly a handle portion, is comprised of a rigid synthetic plastic material with means for connecting switched RF energy to the metal tissue engaging tips. And still another embodiment of the invention, a switch mounted on a rigid conductive hemostat is provided with a switch mounted thereon and insulated from the surgeon's hand by an insulative coating, such as latex.

22 Claims, 4 Drawing Sheets

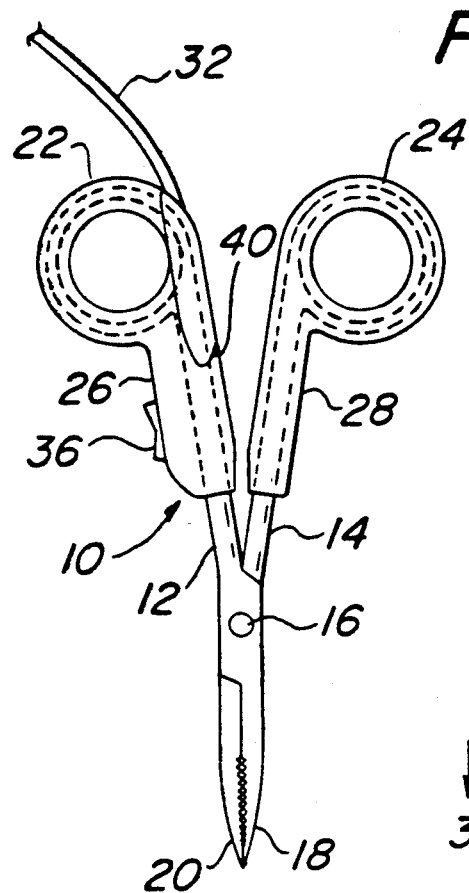
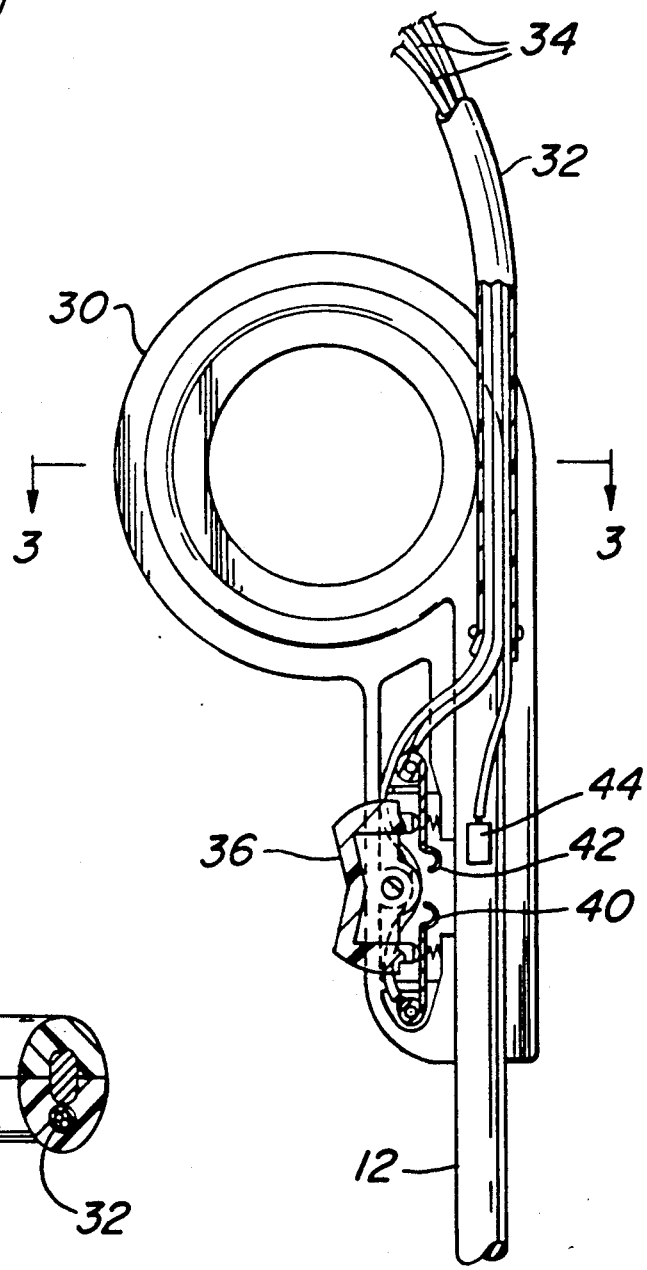

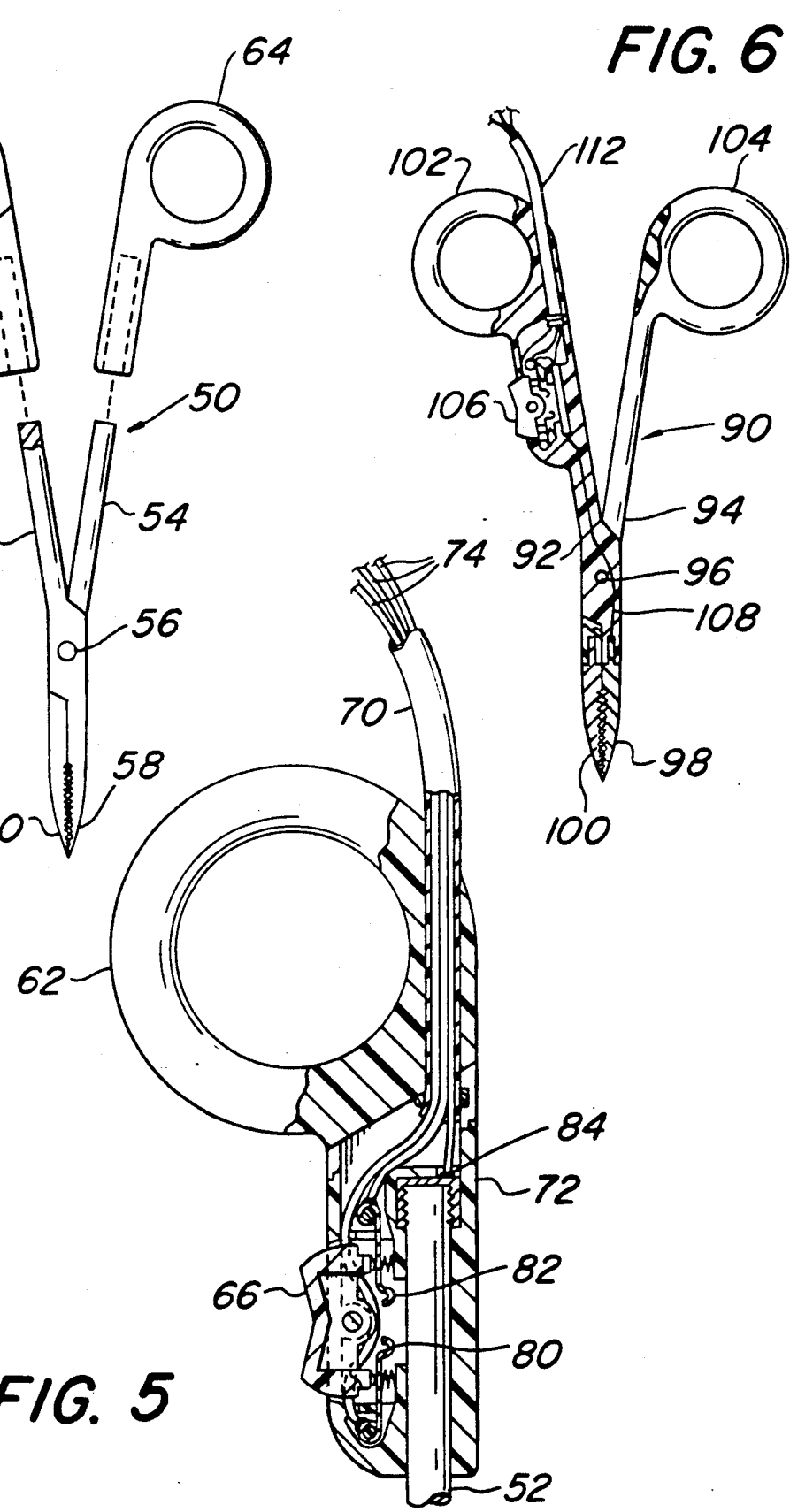

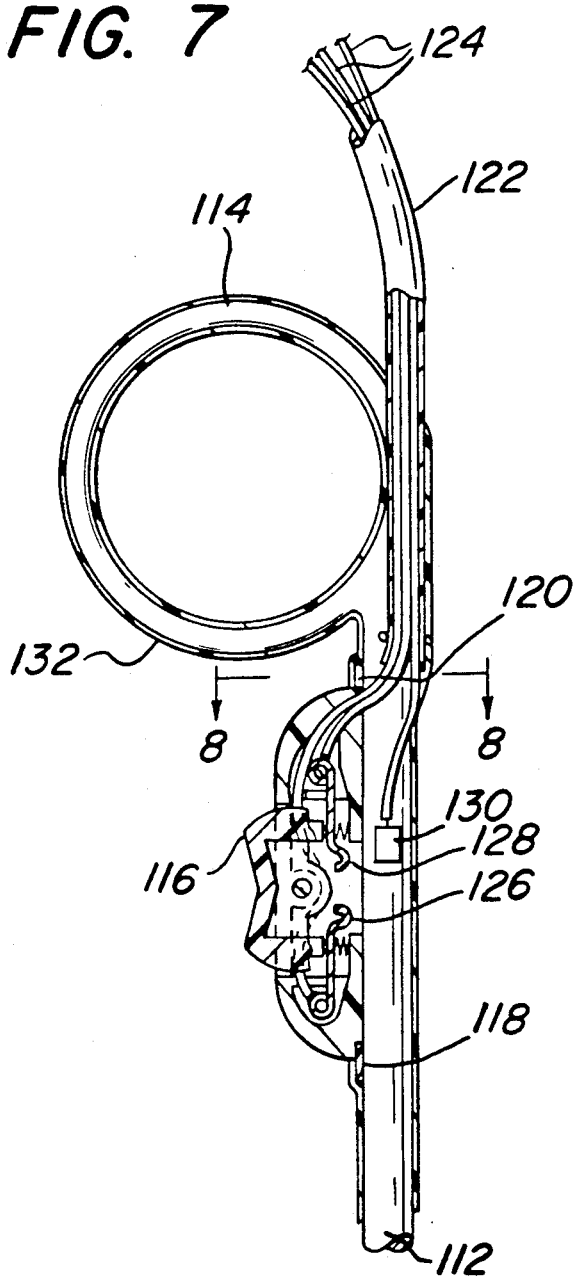
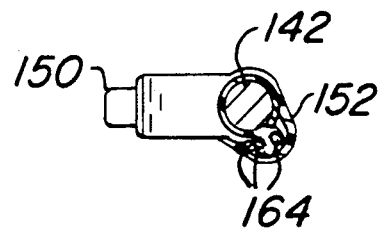
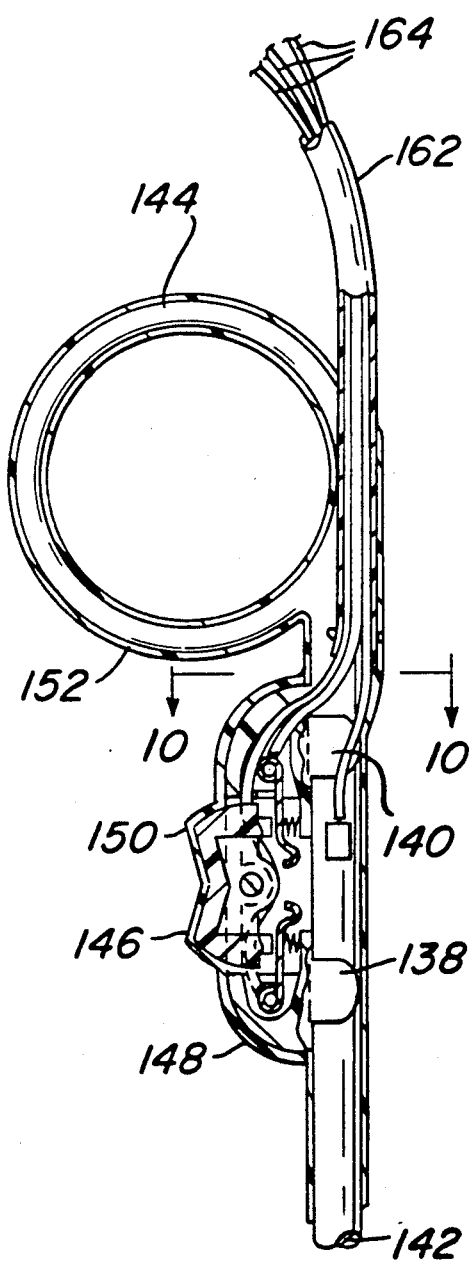
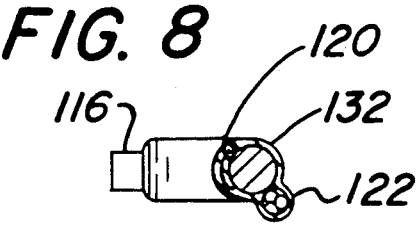

5,116,332

ELECTROCAUTERY HEMOSTAT

CROSS REFERENCE TO RELATED APPLICATIONS

This application is a continuation-in-part application of U.S. patent application Ser. No. 06/881,750 filed Jul. 2, 1986 by the inventor herein and entitled *ELECTROCAUTERY HEMOSTAT* now U.S. Pat. No. 5,026,370; which in turn is a continuation of application Ser. No. 06/663,091, filed Oct. 24, 1984 by the inventor herein and entitled *ELECTROCAUTERY HEMOSTAT*, now abandoned; which in turn is a continuation-in-part application of U.S. patent application Ser. No. 06/443,517 filed Nov. 22, 1982 by the inventor herein and which is entitled *REMOVABLE SWITCH ELECTROCAUTERY INSTRUMENTS*, now U.S. Pat. No. 4,552,143; which in turn is a continuation-in-part patent application of U.S. patent application Ser. No. 06/242,746, filed Mar. 11, 1981 by the inventor herein and which is entitled *ELECTROCAUTERY HEMOSTAT*, now U.S. Pat. No. 4,370,980.

The teachings of all my prior patents are incorporated herein by reference the same as if set forth at length.

BACKGROUND OF THE INVENTION

The present invention is directed to an improved electrocautery instrument which provides certain advantages, particularly with respect to the method of manufacture.

Electrocautery instruments have become widely used in surgery today. Various electrocautery instruments have been patented. Reference may be had to the patents of the inventor herein which are cross referenced above along with the various patent documents cited in these patents.

The present invention provides additional unique structure and methods which enhance the availability of the electrocautery instrument by improving the manufacturing process and reducing the manufacturing cost thereof.

SUMMARY OF THE INVENTION

Briefly, in accordance with the present invention, an improved electrocautery instrument is provided which utilizes in one embodiment a pair of members pivotally connected to each other at a point between the ends of the members, one end of each of the members is provided with a handle and the other end being constructed of metal. A switch means is provided along one member near its handle for controlling electrical energy flow and at least a portion of each pivotal member is constructed of a non-conductive material extending from the handle of each member and being connectable to a metal portion forming the portion of each member extending to the other end. The improved electrocautery instrument also includes means for connecting an electrical output of the switch to the metal end of at least one of the members. The non-conductive material may preferably be rigid and may preferably be comprised of a synthetic plastic material a number of which are well known and commercially available.

In another embodiment, an improved electrocautery hemostat is provided in which a metal hemostat having tissue engaging tips at one end and ring shaped handles at the other end is utilized. A plastic housing is provided over each ring shaped handle of the hemostat and an electrical switch is mounted within one of the plastic housings, the switch is provided with means for connection to an electrical energy source and to the metal hemostat for controlling the application of electrical energy to the metal hemostat.

In a preferred embodiment, the plastic housing mountable over the ring shaped handle is comprised of two mating portions which are substantially in the form of mirror images and which are mounted over at least the ring shaped handles of the hemostat and sonically welded together. The present invention provides advantages wherein efficiency of the manufacturing process may be improved and a large variety of shapes of metal tips may be utilized with a single plastic switch handle assembly.

In still another embodiment, a metallic hemostat is provided with ring handles at one end and tissue engaging tips at the other end. An electrical switch is mounted on one of the members of the hemostat near one of the handles and the ring handles, the electrical switch and at least a portion of the pivotal members extending from the handles to the pivot point are covered with a layer of insulating material, such as latex.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

In view of the above, the present invention may be embodied in other specific forms without departing from the spirit or essential attributes thereof and, accordingly, reference should be made to the appended claims, rather than to the foregoing specification as indicating the scope of the invention.

FIG. 1 is a plan view of one embodiment of an electrocautery hemostat in accordance with the present invention wherein the metal portion of the hemostat within the synthetic housing is shown in dotted lines.

FIG. 2 is a broken away view of the handle portion of the electrocautery hemostat with one half of the synthetic housing removed.

FIG. 3 is a cross sectional view taken along line 3—3 of FIG. 2.

FIG. 4 is a plan view of another embodiment of the present invention showing the metallic portions and the synthetic or plastic portions of the hemostat separated.

FIG. 5 is a broken away view, partially in cross section, of the switch handle portion of the electrocautery hemostat shown in FIG. 4.

FIG. 6 is a plan view, partially in cross section, of another embodiment of the present invention.

FIG. 7 is a partial cross sectional view of a switch handle portion of another embodiment of the hemostat in accordance with the present invention.

FIG. 8 is a cross sectional view taken along line 8—8 of FIG. 7.

FIG. 9 is a partial cross sectional view of another embodiment of the present invention.

FIG. 10 is a cross sectional view taken along line 10—10 of FIG. 9.

DETAILED DESCRIPTION OF THE PREFERRED EMBODIMENTS

Figure 11:
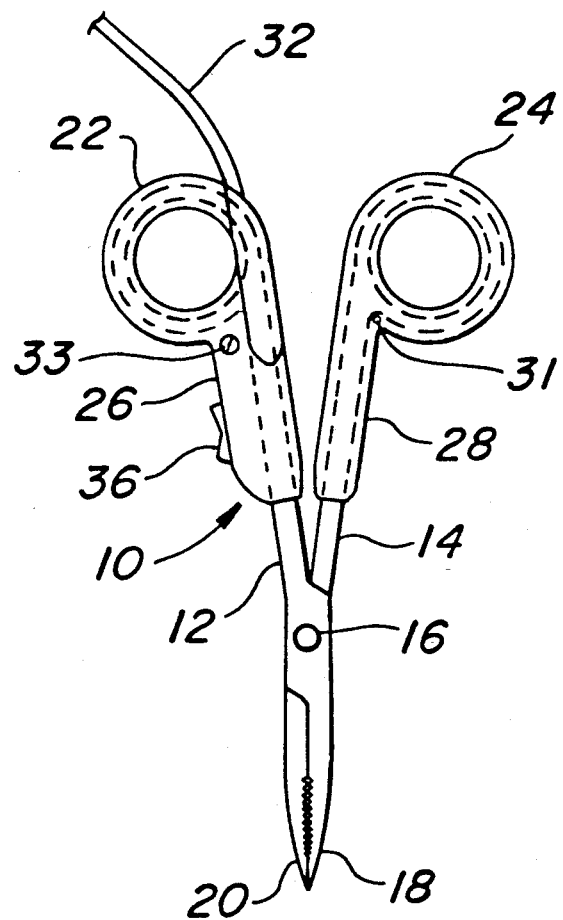
FIG. 11 is a plan view of an electrocautery hemostat in accordance with FIG. 1 illustrating fasteners bonding the two mirror half clam shells together.

Referring now to the drawings in detail, wherein like numerals indicate like elements, there is shown in FIG. 1 a plan view of an electrocautery hemostat 10. Electrocautery hemostat 10 is comprised of a pair of conductive members 12 and 14 pivoted together at pivot point 16 between tissue engaging tips 18 and 20 on the one hand and their respective ring handle ends 22 and 24. The members 12 and 14 are preferably comprised of metal, such as stainless steel, but other suitable rigid conductive materials may be utilized. The ring handles 22 and 24, including a portion of members 12 and 14 extending toward pivot point 16 are covered by housings 26 and 28 which are comprised of a non-conductive, preferably synthetic plastic material. The synthetic housings 26 and 28 are preferably formed, each of two substantially similar mirror images which are joined along the plane passing through the centers of members 12 and 14 and rings 22 and 24. This may also be seen in FIG. 2 wherein one half of synthetic housing 26 has been removed. This type of structure is sometimes referred to as clam shell housings, and this term may be referred to herein. The half of the clam shell in FIG. 2 is given the separate number of 30.

Electrical energy is carried to, and control signals from, electrocautery hemostat 10 via cable or multiconductor wire 32. As may be seen more clearly in FIGS. 2 and 3, multiconductor wire 32 preferably includes 3 separate insulated wire conductors 34. However, depending upon the structure of the source of electrical energy and the details of the switch construction, more or less conductors may be utilized, and it is known that in certain applications with certain equipment which is commercially available, four conductors may be utilized. However, the currently preferred form of commercially available source equipment utilizes three conductors as shown.

The application of electrical energy to tips 18 and 20 is controlled by electrical switch 36. Electrical switch 36 is preferably a bipolar switch which may be utilized to control the application of electrical energy to predetermined values to tips 18 and 20. A lower value is applied for the purpose of coagulation via the process of cauterization and a second and higher value is applied for the purpose of cutting tissue. The energy applied is RF energy as provided by commercially available equipment on the market such as that available from Valleylab, Inc. of Boulder, Colo. As is well known in the industry, one of each of the switch terminals is connected to a coagulation line connected to terminal 42, the other is connected to a cut line connected to terminal 40 and the third wire is connected to the metallic member of the electrocautery hemostat which is connected to an active lead line at connection 44. There is also a return line connected to the equipment from a contact placed in contact with the patient, usually under the patient, during the surgical operation.

As may be seen from FIGS. 1 through 3, the wire 32 enters along ring handle 22 and runs along member 12 for a short distance to switch 36. The wire running along ring handle 22 and member 12 may require a slight proturbance of clam shell 38 as seen at 40 in FIG. 1.

Figure 12:
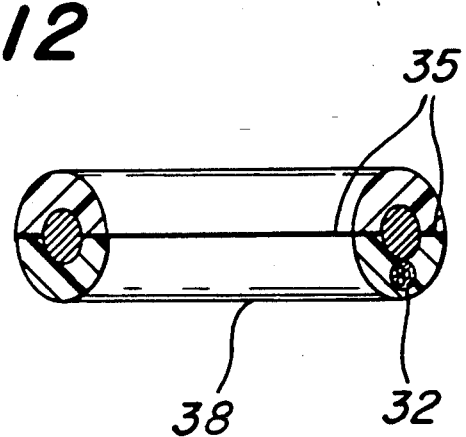
FIG. 12 is a cross sectional view similar to that of FIG. 3 illustrating bonding of the two mirror half clam shells together by adhesive bonding.

One of the advantages of the embodiment shown in FIGS. 1 through 3 is the ease of manufacture and the reduction of manufacturing costs. In this embodiment, a standard metallic hemostat, such as preferably a stainless steel hemostat, which may be obtainable from various sources, particularly imported, at very reasonable costs. The mirrored clam shell housings for ring 22 on member 12, with the switch prefabricated therein, may be readily assembled over the portion of member 12 and ring 22 and sonically welded together along the mating plane. Of course, other forms of bonding the two mirror half clam shells together, such as adhesive bonding, riveting or threaded fasteners, may be readily utilized. FIG. 11 illustrates bonding in the form of rivets 31, a threaded fastener or screw 33. FIG. 12 illustrates adhesive at 35 bonding the two mirror half clam shells together. However, the presently prefered method is that of sonic welding. In a like manner, the clam shells for ring 24 and the portion of member 14 may be readily joined over ring 24 and a portion of member 14 and sonically welded.

Referring now to FIG. 4, there is shown another embodiment of the present invention wherein the electrocautery hemostat is comprised of a metallic portion and the handles and switch mechanism are comprised of a synthetic plastic housing. In the embodiment shown in FIG. 4, the hemostat 50 is comprised of metallic members 52 and 54 pivoted together at pivot point 56. Members 52 and 54 are provided with tissue engaging tips 58 and 60 respectively. Members 52 and 54 are preferably comprised of a metal such as stainless steel but other rigid conducting materials may be utilized. The electrocautery hemostat is shown in FIG. 4 with metallic members 52 and 54 disassembled from the ring shaped synthetic plastic handles 62 and 64. Handle 62 is provided with a switch 66 mounted therein. Electrical energy is carried to the electrocautery hemostat via cable or multiconductor wire 70. In manufacturing, the ring shaped handles 62 and 64 with switch 66 may be prefabricated. The members 52 and 54 may be simply inserted into handles 62 and 64, respectively, and automatically engaged therein by a retaining means 72 which may be a tubular member having serrated teeth or other means for engaging the metallic members. Retaining means 72 also forms one of the electrical contacts between one of the electrical conductors 74 and member 52 as shown in FIG. 5. This particular embodiment provides the advantage of being able to fabricate different embodiments of electrocautery hemostat including right and left angle hemostats utilizing the same handles, with merely differing metallic portions being inserted therein or, said differently, standard handles being inserted on differing pivoted metallic members having the desired tips.

Further detail of the structure of handle member 62 and switch 66 is shown in FIG. 5. In a manner similar to that described with respect to FIGS. 1-3, and with respect to the remaining embodiments herein, the cable carrying electrical energy and control signals between the electrocautery hemostat and the electrocautery instrument is preferably comprised of three leads or insulated wires 74 which includes a wire connected to cut terminal 80, a wire connected to coagulation terminal 82 and a connection 84 directly to the retaining means 72 which holds member 52.

There is shown in FIG. 6 another variation of the embodiment 90 of FIGS. 4 and 5 wherein the major portion of the electrocautery instrument is fabricated from a rigid plastic synthetic material to form members 92 and 94. Plastic synthetic members 92 and 94 are pivotally connected together at pivot point 96 and are provided with metallic tips 98 and 100. Members 92 and 94 are provided with ring shaped handles 102 and 104, both made of synthetic plastic material. Member 92 is also provided with a switch for controlling the flow and the amount of electrical energy to the tips 98 and 100. The electrical energy and control signals are carred to and from the instrument via multiconductor cable 112 as described with respect to the embodiments shown in FIGS. 1 through 5. Energy is carred from electrical switch 106 to metallic tip 98 via a conductor 108 which may be embedded within member 92.

Referring now to FIG. 7, there is shown a broken away view of the switch handle of another embodiment of the present invention wherein the electrocautery hemostat is comprised of a metallic hemostat which may be of somewhat conventional construction, namely entirely of stainless steel, to which a switch is fabricated as discussed hereinafter and to which a handle portion of the hemostat is covered with an insulative covering, such as latex. Member 112 is comprised of a conductor, preferably metal, and preferably stainless steel, but it is understood that other rigid conductors may be utilized. Member 112 is provided with a ring handle 114. The overall shape of the hemostat is similar to that shown in FIG. 6 and the other embodiments contained herein. A switch 116 is mounted to member 112 by tabs 118 and 120. The tabs may be spot welded to member 112 or bonded thereto by other suitable means including adhesive bonding. In a manner similar to the other embodiments described herein, electrical energy and control signals are transferred between the electrocautery hemostat and the electrocautery source equipment via cable 122 which is a multiconductor cable as shown at 124. One of the wires is connected to terminal 126, another wire is connected to coagulation terminal 128 and a third lead, sometimes referred to as the active lead, is connected directly to member 112 at connection 130.

A substantial portion of member 112 including ring handle 114 is covered by an insulative coating 132, which may be latex or other suitable insulative material which may be readily applied to the portions of the hemostat which usually come in contact with the surgeon's hands. The insulative coating 132, switch 116 and cable 122 running within the insulative covering 132 as well as switch mounting member 120 are shown in the cross sectional view in FIG. 8.

Referring now to FIGS. 9 and 10, there is another variation of the embodiment of the invention shown in FIGS. 7 and 8 wherein an alternative mounting means is shown for the switch in the form of clips 138 and 140. As with FIG. 7, the embodiment of FIG. 10 is comprised of a metallic hemostat in which switch handle member 142 having ring handle 144 is shown in FIG. 9. The handle portions and a substantial portion of the member extending down toward the pivot points are covered with an insulative covering 152. The insulative covering 152 as illustrated in FIG. 9 also completely covers switch 146 as shown at 148 and 150. Multiconductor cable 162 having multiple insulative leads 164 supplies energy and control signals between the instrument and the supply equipment in the same manner as described with respect to the previous embodiments.

It will be apparent to those skilled in the art that numerous modifications and variations may be made to the present invention without departing from the scope of the present invention. Although presently preferred forms of the present invention have been disclosed herein, various modifications are readily apparent. For example, although it is presently preferred that ring shaped handles be provided for ease of use, enhanced control during surgical operations and to provide an instrument having a shape which surgeons are accustomed to using, therefore making it more valuable immediately and not requiring a learning curve, it will be apparent to those skilled in the art that the ring shaped handled could be eliminated and other shapes of handles may be utilized including curved or saddle shaped handles which would be adapted to the shape of the finger with various types of spring loaded mechanisms so that the pivotal members could be operated merely by pressing the handles together. Further, although the invention may be described in terms of a metal conductive member or members, it is apparent that any other suitable conductive material may be utilized in the practicing of the invention, including conductive materials which may be in the form of doped plastics which provide sufficient conductivity. Other suitable conductive materials may be utilized. Further, although rigid members are preferred, it is understood that full rigidity is not required, particularly as the instrument is an electrocautery instrument not requiring the blood vessel compression forces which might be required in an ordinary hemostat. Additionally, although clam shell and other nonconductive members described herein are preferably comprised of well known synthetic plastic materials which are now commercially available, it is understood that other non-conductive materials may be utilized in practicing the present invention, including materials such as rubber, hard rubber and various other material known as non-conductors whether or not they specifically fit into the category of plastic synthetic materials. In summary, various modifications may be made within the spirit and scope of the present invention without departing therefrom.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. An electrocautery instrument, comprising:
   a pair of members pivotally connected to each other at a point between the ends of each member, one end of each member being provided with a non-conductive handle and the other end being constructed of a conductive material;
   a switch means for controlling electrical energy flow being provided along one member near the handle provided for the member;
   at least a portion of each pivotal member being constructed of a non-conductive material extending from the handle of each member and being connectable to a conductive portion forming the portion of each member extending to the other end of each member; and
   means for connecting an electrical output of said switch to the conductive end of at least one of said members such that said electrical energy flow is primarily from said conductive end to a patient's tissue.

2. An electrocautery instrument in accordance with claim 1 wherein said non-conductive material is a rigid material.

3. An electrocautery instrument in accordance with claim 1 wherein said non-conductive material is comprised of a synthetic plastic material.

4. An electrocautery instrument in accordance with claim 1 wherein said switch means includes means for selecting the application of electrical energy in different modes, including an electrocauterization mode and a cut mode.

5. An electrocautery instrument in accordance with claim 1 wherein said portion of the pivotal member constructed of non-conductive material extends from said handle to a point before the pivotal connection.

6. An electrocautery instrument in accordance with claim 5 wherein the other ends constructed of conductive material are inserted into a receptacle in the non-conductive material extending from the handle and said means for connecting the electrical output of the switch is comprised of a conductive area of contact connected to said switch which engages the inserted conductive member.

7. An electrocautery instrument in accordance with claim 1 wherein said portion of each member constructed of non-conductive material extends from the handle of each member to a point beyond the point at which the members are pivotally connected together.

8. An electrocautery instrument in accordance with claim 7 wherein said means for connecting the electrical output of said switch to the conductive material in the form of a metal tip of at least one of said members is comprised of an electrical conductor imbedded within the non-conductive material.

9. An electrocautery instrument in accordance with claim 7 wherein the ends constructed of conductive material is comprised of conductive tips which are inserted into the non-conductive members beyond the pivot point.

10. An electrocautery instrument in accordance with claim 9 wherein said conductive tip is comprised of a metal.

11. An electrocautery hemostat, comprising:
a metal hemostat having tissue engaging tips at one end and handles at the other end;
a non-conductive housing mountable over at least each handle of said hemostat;
an electrical switch mounted within one of said non-conductive housings, said switch being provided with means for connection to an electrical energy source and to said metal hemostat for controlling the application of electrical energy to said metal hemostat and with flow of said electrical energy being primarily from said metal tips to said tissue.

12. An electrocautery hemostat in accordance with claim 11 wherein said hemostat includes metal members extending from said handles to said tips and pivotable at a point between said tips and said handles, said non-conductive housing extending over at least a portion of said metallic members extending from said handles.

13. An electrocautery hemostat in accordance with claim 11 wherein said non-conductive housing is comprised of two mating portions, which are substantially in the form of mirror images and which are mounted over at least the handles of said hemostat and sonically welded together.

14. An electrocautery hemostat in accordance with claim 11 wherein said non-conductive housing is comprised of two mating portions, which are substantially in the form of mirror images and which are mounted over at least the handles of said hemostat and joined by adhesive bonding.

15. An electrocautery hemostat in accordance with claim 11 wherein said non-conductive housing is comprised of two mating portions, which are substantially in the form of mirror images and which are mounted over at least the handles of said hemostat and joined by at least one fastener.

16. An electrocautery hemostat in accordance with claim 11 wherein said non-conductive housing is comprised of a synthetic plastic material.

17. An electrocautery hemostat in accordance with claim 11 wherein said handles are ring shaped.

18. An electrocautery hemostat in accordance with claim 11 wherein said electrical switch is provided with at least two contacts, one utilized for application of energy of a first predetermined magnitude for the purpose of coagulation and a second contact for the application of energy of a second predetermined value for cutting tissue.

19. An electrocautery hemostat, comprising:
a metal hemostat having tissue engaging tips at one end and handles at the other end, said hemostat being comprised of two metal arms pivoted between said ends;
an electrical switch mounted on one of said members, said switch being provided with means for connection to an electrical energy source and to said metal hemostat for controlling the application of electrical energy to said metal hemostat and with flow of said electrical energy being primarily from said metal tips to said tissue; and
an insulative coating applied over at least said handles, at least a portion of said electrical switch and at least a portion of said members extending from said handles to said pivot point.

20. An electrocautery hemostat in accordance with claim 19 wherein said electrical switch is provided with at least two contacts, one utilized for application of energy of a first predetermined magnitude for the purpose of coagulation and a second contact for the application of energy of a second predetermined value for cutting tissue.

21. An electrocautery hemostat in accordance with claim 19 wherein said handles are ring shaped.

22. An electrocautery hemostat in accordance with claim 19 wherein said insulative coating is applied over all of said electrical switch.

* * * * *

UNITED STATES PATENT AND TRADEMARK OFFICE
CERTIFICATE OF CORRECTION

PATENT NO. : 5,116,332
DATED : May 26, 1992
INVENTOR(S) : Edward A. Lottick

It is certified that error appears in the above-identified patent and that said Letters Patent is hereby corrected as shown below:

Column 7, line 47: delete "the other" and insert --another--.

Column 8, line 47: delete "members" and insert --metal arms--.

Signed and Sealed this

Thirteenth Day of July, 1993

Attest:

MICHAEL K. KIRK

*Attesting Officer*      *Acting Commissioner of Patents and Trademarks*